United States Patent
Kinio et al.

(10) Patent No.: US 12,246,148 B2
(45) Date of Patent: *Mar. 11, 2025

(54) METHODS FOR DETERMINING A POSITION OF A FIRST MEDICAL DEVICE WITH RESPECT TO A SECOND MEDICAL DEVICE, AND RELATED SYSTEMS AND MEDICAL DEVICES

(71) Applicant: Boston Scientific Medical Device Limited, Galway (IE)

(72) Inventors: Steven Kinio, Mississauga (CA); Gareth Davies, Toronto (CA); Laurentiu Murtescu, Maple (CA)

(73) Assignee: Boston Scientific Medical Device Limited, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/342,353

(22) Filed: Jun. 27, 2023

(65) Prior Publication Data

US 2023/0338710 A1 Oct. 26, 2023

Related U.S. Application Data

(62) Division of application No. 16/720,212, filed on Dec. 19, 2019, now Pat. No. 11,724,070.

(51) Int. Cl.
*A61B 17/34* (2006.01)
*A61B 17/32* (2006.01)
(Continued)

(52) U.S. Cl.
CPC ......... *A61M 25/0606* (2013.01); *A61B 17/32* (2013.01); *A61B 17/34* (2013.01);
(Continued)

(58) Field of Classification Search
CPC ..... A61B 5/053; A61B 5/0538; A61B 5/6848; A61B 5/0531; A61B 5/0535; A61B 5/05;
(Continued)

(56) References Cited

U.S. PATENT DOCUMENTS

| | | |
|---|---|---|
| 175,254 A | 3/1876 | Oberly |
| 827,626 A | 7/1906 | Gillet |

(Continued)

*Primary Examiner* — Majid Jamialahmadi
(74) *Attorney, Agent, or Firm* — Nelson Mullins Riley & Scarborough LLP

(57) ABSTRACT

A system of medical devices includes a first medical device, a second medical device, an RLC circuit, a processor, and an output device. The first medical device includes an elongate member having a lumen. The second medical device includes a needle advanceable through the lumen. The RLC circuit includes an excitation voltage source, a resistor, a capacitor, an inductor, and an output voltage sensor. The inductor includes a coil that is supported by the first medical device and wound around the lumen. As the needle is advanced through the lumen, an output voltage of the RLC circuit is an indicator of a longitudinal position of the needle with respect to the elongate member. The voltage sensor is configured to sense the output voltage, and the processor and output device are configured to generate an output that is an indicator of the longitudinal position of the needle.

13 Claims, 12 Drawing Sheets

(51) Int. Cl.
*A61B 90/00* (2016.01)
*A61M 25/06* (2006.01)

(52) U.S. Cl.
CPC ... *A61B 17/3403* (2013.01); *A61B 2090/0811* (2016.02); *A61M 2205/0238* (2013.01); *A61M 2205/0288* (2013.01); *A61M 2205/3306* (2013.01); *A61M 2205/3317* (2013.01); *A61M 2205/50* (2013.01); *A61M 2205/502* (2013.01); *A61M 2205/587* (2013.01)

(58) Field of Classification Search
CPC ....... A61B 5/061; A61B 5/742; A61B 5/7425; A61B 5/743; A61B 5/7435; A61B 5/744; A61B 5/7445; A61B 17/3403; A61B 17/34; A61B 2017/3407; A61B 2017/3409; A61B 2017/3411; A61B 2017/3413; A61B 2090/0811
See application file for complete search history.

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |

(56) References Cited

U.S. PATENT DOCUMENTS

| | | | |
|---|---|---|---|
| 6,283,983 B1 | 9/2001 | Makower et al. | |
| 6,292,678 B1 | 9/2001 | Hall et al. | |
| 6,293,945 B1 | 9/2001 | Parins et al. | |
| 6,296,615 B1 | 10/2001 | Brockway et al. | |
| 6,296,636 B1 | 10/2001 | Cheng et al. | |
| 6,302,898 B1 | 10/2001 | Edwards et al. | |
| 6,304,769 B1 | 10/2001 | Arenson et al. | |
| 6,315,777 B1 | 11/2001 | Comben | |
| 6,328,699 B1 | 12/2001 | Eigler et al. | |
| 6,337,994 B1 * | 1/2002 | Stoianovici | A61B 5/0538 600/373 |
| 6,360,128 B2 | 3/2002 | Kordis et al. | |
| 6,364,877 B1 | 4/2002 | Goble et al. | |
| 6,385,472 B1 | 5/2002 | Hall et al. | |
| 6,394,976 B1 | 5/2002 | Winston et al. | |
| 6,395,002 B1 | 5/2002 | Ellman et al. | |
| 6,419,674 B1 | 7/2002 | Bowser et al. | |
| 6,428,551 B1 | 8/2002 | Hall et al. | |
| 6,450,989 B2 | 9/2002 | Dubrul et al. | |
| 6,475,214 B1 | 11/2002 | Moaddeb | |
| 6,485,485 B1 | 11/2002 | Winston et al. | |
| 6,508,754 B1 | 1/2003 | Liprie et al. | |
| 6,524,303 B1 | 2/2003 | Garibaldi | |
| 6,530,923 B1 | 3/2003 | Dubrul et al. | |
| 6,554,827 B2 | 4/2003 | Chandrasekaran et al. | |
| 6,562,031 B2 | 5/2003 | Chandrasekaran et al. | |
| 6,562,049 B1 | 5/2003 | Norlander et al. | |
| 6,565,562 B1 | 5/2003 | Shah et al. | |
| 6,607,529 B1 | 8/2003 | Jones et al. | |
| 6,632,222 B1 | 10/2003 | Edwards et al. | |
| 6,639,999 B1 | 10/2003 | Cookingham et al. | |
| 6,650,923 B1 | 11/2003 | Lesh et al. | |
| 6,651,672 B2 | 11/2003 | Roth | |
| 6,662,034 B2 | 12/2003 | Segner et al. | |
| 6,663,621 B1 | 12/2003 | Winston et al. | |
| 6,702,811 B2 | 3/2004 | Stewart et al. | |
| 6,709,444 B1 | 3/2004 | Makower | |
| 6,723,052 B2 | 4/2004 | Mills | |
| 6,733,511 B2 | 5/2004 | Hall et al. | |
| 6,740,103 B2 | 5/2004 | Hall et al. | |
| 6,752,800 B1 | 6/2004 | Winston et al. | |
| 6,755,816 B2 | 6/2004 | Ritter et al. | |
| 6,811,544 B2 | 11/2004 | Schaer | |
| 6,814,733 B2 | 11/2004 | Schwartz et al. | |
| 6,820,614 B2 | 11/2004 | Bonutti | |
| 6,834,201 B2 | 12/2004 | Gillies et al. | |
| 6,842,639 B1 | 1/2005 | Winston et al. | |
| 6,852,109 B2 | 2/2005 | Winston et al. | |
| 6,855,143 B2 | 2/2005 | Davison et al. | |
| 6,860,856 B2 | 3/2005 | Ward et al. | |
| 6,869,431 B2 | 3/2005 | Maguire et al. | |
| 6,911,026 B1 | 6/2005 | Hall et al. | |
| 6,951,554 B2 | 10/2005 | Johansen et al. | |
| 6,951,555 B1 | 10/2005 | Suresh et al. | |
| 6,955,675 B2 | 10/2005 | Jain | |
| 6,970,732 B2 | 11/2005 | Winston et al. | |
| 6,980,843 B2 | 12/2005 | Eng et al. | |
| 7,029,470 B2 | 4/2006 | Francischelli et al. | |
| 7,056,294 B2 | 6/2006 | Khairkhahan et al. | |
| 7,083,566 B2 | 8/2006 | Tornes et al. | |
| 7,112,197 B2 | 9/2006 | Hartley et al. | |
| 7,335,197 B2 | 2/2008 | Sage et al. | |
| 7,618,430 B2 | 11/2009 | Scheib | |
| 7,651,492 B2 | 1/2010 | Wham | |
| 7,666,203 B2 | 2/2010 | Chanduszko et al. | |
| 7,678,081 B2 | 3/2010 | Whiting et al. | |
| 7,682,360 B2 | 3/2010 | Guerra | |
| 7,828,796 B2 | 11/2010 | Wong et al. | |
| 7,900,928 B2 | 3/2011 | Held et al. | |
| 8,192,425 B2 | 6/2012 | Mirza et al. | |
| 8,257,323 B2 | 9/2012 | Joseph et al. | |
| 8,388,549 B2 | 3/2013 | Paul et al. | |
| 8,500,697 B2 | 8/2013 | Kurth et al. | |
| 11,339,579 B1 | 5/2022 | Stearns | |
| 2001/0012934 A1 | 8/2001 | Chandrasekaran et al. | |
| 2001/0021867 A1 | 9/2001 | Kordis et al. | |
| 2002/0019644 A1 | 2/2002 | Hastings et al. | |
| 2002/0022781 A1 | 2/2002 | McIntire et al. | |
| 2002/0022836 A1 | 2/2002 | Goble et al. | |
| 2002/0035361 A1 | 3/2002 | Houser et al. | |
| 2002/0087153 A1 | 7/2002 | Roschak et al. | |
| 2002/0087156 A1 | 7/2002 | Maguire et al. | |
| 2002/0111618 A1 | 8/2002 | Stewart et al. | |
| 2002/0123749 A1 | 9/2002 | Jain | |
| 2002/0147485 A1 | 10/2002 | Mamo et al. | |
| 2002/0169377 A1 | 11/2002 | Khairkhahan et al. | |
| 2002/0188302 A1 | 12/2002 | Berg et al. | |
| 2002/0198521 A1 | 12/2002 | Maguire | |
| 2003/0032929 A1 | 2/2003 | McGuckin | |
| 2003/0040742 A1 | 2/2003 | Underwood et al. | |
| 2003/0144658 A1 | 7/2003 | Schwartz et al. | |
| 2003/0158480 A1 | 8/2003 | Tornes et al. | |
| 2003/0163153 A1 | 8/2003 | Scheib | |
| 2003/0225392 A1 | 12/2003 | McMichael et al. | |
| 2004/0015162 A1 | 1/2004 | McGaffigan | |
| 2004/0024396 A1 | 2/2004 | Eggers | |
| 2004/0030328 A1 | 2/2004 | Eggers et al. | |
| 2004/0044350 A1 | 3/2004 | Martin et al. | |
| 2004/0073243 A1 | 4/2004 | Sepetka et al. | |
| 2004/0077948 A1 | 4/2004 | Molante et al. | |
| 2004/0116851 A1 | 6/2004 | Johansen et al. | |
| 2004/0127963 A1 | 7/2004 | Uchida et al. | |
| 2004/0133113 A1 | 7/2004 | Krishnan | |
| 2004/0133130 A1 | 7/2004 | Ferry et al. | |
| 2004/0143256 A1 | 7/2004 | Bednarek | |
| 2004/0147950 A1 | 7/2004 | Mueller et al. | |
| 2004/0181213 A1 | 9/2004 | Gondo | |
| 2004/0230188 A1 | 11/2004 | Cioanta et al. | |
| 2005/0004585 A1 | 1/2005 | Hall et al. | |
| 2005/0010208 A1 | 1/2005 | Winston et al. | |
| 2005/0049628 A1 | 3/2005 | Schweikert et al. | |
| 2005/0059966 A1 | 3/2005 | McClurken et al. | |
| 2005/0065507 A1 | 3/2005 | Hartley et al. | |
| 2005/0085806 A1 | 4/2005 | Auge et al. | |
| 2005/0096529 A1 | 5/2005 | Cooper et al. | |
| 2005/0101984 A1 | 5/2005 | Chanduszko et al. | |
| 2005/0119556 A1 | 6/2005 | Gillies et al. | |
| 2005/0137527 A1 | 6/2005 | Kunin | |
| 2005/0149012 A1 | 7/2005 | Penny et al. | |
| 2005/0203504 A1 | 9/2005 | Wham et al. | |
| 2005/0203507 A1 | 9/2005 | Truckai et al. | |
| 2005/0261607 A1 | 11/2005 | Johansen et al. | |
| 2005/0288631 A1 | 12/2005 | Lewis et al. | |
| 2006/0041253 A1 | 2/2006 | Newton et al. | |
| 2006/0074398 A1 | 4/2006 | Whiting et al. | |
| 2006/0079769 A1 | 4/2006 | Whiting et al. | |
| 2006/0079787 A1 | 4/2006 | Whiting et al. | |
| 2006/0079884 A1 | 4/2006 | Manzo et al. | |
| 2006/0085054 A1 | 4/2006 | Zikorus et al. | |
| 2006/0089638 A1 | 4/2006 | Carmel et al. | |
| 2006/0106375 A1 | 5/2006 | Werneth et al. | |
| 2006/0135962 A1 | 6/2006 | Kick et al. | |
| 2006/0142756 A1 | 6/2006 | Davies et al. | |
| 2006/0189972 A1 | 8/2006 | Grossman | |
| 2006/0241586 A1 | 10/2006 | Wilk | |
| 2006/0247672 A1 | 11/2006 | Mdlund et al. | |
| 2006/0264927 A1 | 11/2006 | Ryan | |
| 2006/0276710 A1 | 12/2006 | Krishnan | |
| 2007/0060879 A1 | 3/2007 | Weitzner et al. | |
| 2007/0066975 A1 | 3/2007 | Wong et al. | |
| 2007/0118099 A1 | 5/2007 | Trout | |
| 2007/0123964 A1 | 5/2007 | Davies et al. | |
| 2007/0167775 A1 | 7/2007 | Kochavi et al. | |
| 2007/0208256 A1 | 9/2007 | Marilla | |
| 2007/0225681 A1 | 9/2007 | House | |
| 2007/0270791 A1 | 11/2007 | Wang et al. | |
| 2008/0039865 A1 | 2/2008 | Shaher et al. | |
| 2008/0042360 A1 | 2/2008 | Veikley | |
| 2008/0086120 A1 | 4/2008 | Mirza et al. | |
| 2008/0097213 A1 | 4/2008 | Carlson et al. | |
| 2008/0108987 A1 | 5/2008 | Bruszewski et al. | |
| 2008/0146918 A1 | 6/2008 | Magnin et al. | |
| 2008/0171934 A1 | 7/2008 | Greenan et al. | |
| 2008/0208121 A1 | 8/2008 | Youssef et al. | |

(56) References Cited

U.S. PATENT DOCUMENTS

| | | |
|---|---|---|
| 2008/0275439 A1 | 11/2008 | Francischelli et al. |
| 2009/0105742 A1 | 4/2009 | Kurth et al. |
| 2009/0138009 A1 | 5/2009 | Mswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

\* cited by examiner

METHODS FOR DETERMINING A POSITION OF A FIRST MEDICAL DEVICE WITH RESPECT TO A SECOND MEDICAL DEVICE, AND RELATED SYSTEMS AND MEDICAL DEVICES

CROSS REFERENCE TO RELATED APPLICATIONS

The present application is a divisional of U.S. patent application Ser. No. 16/720,212, filed Dec. 19, 2019, the entire disclosure of which is incorporated herein in its entirety.

FIELD

This document relates to medical devices. More specifically, this document relates to methods for determining a position of a first medical device with respect to a second medical device, and related systems and medical devices.

SUMMARY

The following summary is intended to introduce the reader to various aspects of the detailed description, but not to define or delimit any invention.

Systems of medical devices are disclosed. According to some aspects, a system of medical devices includes a first medical device including an elongate member. The elongate member has a proximal portion defining a proximal end, a distal portion defining a distal end, and a lumen extending longitudinally therethrough from the proximal end to the distal end. The system further includes a second medical device including a needle advanceable through the lumen from the proximal end towards the distal end. The system further includes at least a first RLC circuit including an excitation voltage source, a resistor, a capacitor, an inductor, and an output voltage sensor. The inductor includes a coil that is supported by the first medical device and wound around the lumen. As the needle is advanced through the lumen, an output voltage of the RLC circuit is an indicator of a longitudinal position of the needle with respect to the elongate member. The voltage sensor is configured to sense the output voltage of the RLC circuit and generate a sensor signal based on the output voltage. A processor is in communication with the voltage sensor and is configured to receive and process the sensor signal from the voltage sensor, and generate a processor signal based on the sensor signal. An output device is in communication with the processor and is configured to receive the processor signal and generate an output based on the processor signal. The output is an indicator of the longitudinal position of the needle with respect to the elongate member.

In some examples, the elongate member includes a sidewall extending longitudinally between the proximal end and the distal end, and radially between an inner surface and an outer surface, and the coil is embedded in the sidewall.

In some examples, the inductor further includes a magnetic core positioned radially inwardly of the coil and supported by the first medical device. The magnetic core can be embedded in the sidewall.

In some examples, the inductor further includes a magnetic core, and the magnetic core is provided by a magnetic coating on the needle. In some examples, the needle is fabricated from a magnetic material to provide a magnetic core of the inductor.

In some examples, the coil extends continuously from the proximal portion to the distal portion. In some examples, the coil is positioned within the distal portion, proximate the distal end.

In some examples, the system further includes a second RLC circuit including a second excitation voltage source, a second resistor, a second capacitor, a second inductor comprising a second coil, and a second output voltage sensor. The second coil can be supported by the first medical device, wound around the lumen, and spaced proximally from the coil of the first RLC circuit. As the needle is advanced through the lumen, an output voltage of the second RLC circuit can be an additional indicator of the longitudinal position of the needle with respect to the elongate member.

In some examples, the output device includes at least one of a light and a screen. The output can include illumination of the light when the needle is at a predetermined longitudinal position with respect to the elongate member. The output can include a GUI showing an image of the longitudinal position of the needle with respect to the elongate member.

Methods for determining a position of a first medical device with respect to a second medical device are also disclosed. According to some aspects, a method for determining a position of a first medical device with respect to a second medical device includes: a. advancing the second medical device into a lumen of the first medical device, from a proximal end of the first medical device towards a distal end of the first medical device; b. during step a., applying an excitation voltage to an RLC circuit associated with the first medical device, and sensing an output voltage of the RLC circuit, whereby the output voltage is an indicator of a longitudinal position of the second medical device with respect to the first medical device; and c. generating an output based on the output voltage, wherein the output is an indicator of the longitudinal position of the second medical device with respect to the first medical device.

In some examples, step a. includes passing the second medical device through a coil of an inductor of the RLC circuit.

In some examples, step c. includes generating an image of the longitudinal position of the second medical device with respect to the first medical device, and updating the image as the output voltage changes.

In some examples, the method further includes adjusting a position of the second medical device with respect to the first medical device based on the output.

Medical devices are also disclosed. According to some aspects, a medical device includes an elongate member having a proximal portion defining a proximal end, a distal portion defining a distal end, a sidewall extending longitudinally between the proximal end and the distal end and radially between an inner surface that and an outer surface, and a lumen defined by the inner surface and extending longitudinally through the elongate member from the proximal end to the distal end. The medical device further includes an inductor including a coil embedded in the sidewall and wound around the lumen. The coil is electrically connectable to an excitation voltage source, a resistor, a capacitor, and an output voltage sensor to form an RLC circuit.

In some examples, the inductor further includes a magnetic core positioned radially inwardly of the coil and supported by the elongate member. The magnetic core can be embedded in the sidewall.

In some examples, the coil extends continuously from the proximal portion to the distal portion. In some examples, the coil is positioned within the distal portion, proximate the distal end.

In some examples, the device includes a second inductor. The second inductor can include a second coil embedded in the sidewall and wound around the lumen. The second coil can be spaced proximally from the coil of the first RLC circuit. The second coil can be electrically connectable to a second excitation voltage source, a second resistor, and a second output voltage sensor to form a second RLC circuit.

BRIEF DESCRIPTION OF THE DRAWINGS

The accompanying drawings are for illustrating examples of articles, methods, and apparatuses of the present disclosure and are not intended to be limiting. In the drawings.

DETAILED DESCRIPTION

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all of the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are systems of medical devices, where the systems include an RLC circuit (i.e. at least one RLC circuit). The RLC circuit can be used to determine a position of a first medical device of the system with respect to a second medical device of the system. For example, a system of medical devices can include a first medical device (e.g. a catheter in the form of a sheath or dilator) that in use is advanced into a patient's body to a target location (e.g. advanced via a femoral vein to a patient's heart) and a second medical device (e.g. a perforation device including a needle) that in use is passed through the first medical device towards the target location. The inductor of the RLC circuit can include a coil that that is wound so that as the second medical device is passed through the first medical device, it passes through the coil. In use, an excitation voltage can be applied to the RLC circuit, and an output voltage of the RLC circuit can be sensed and monitored. Passage of the second medical device through the coil can change the inductance of the inductor and thus change the output voltage of the RLC circuit (e.g. the output voltage can become non-resonant). The output voltage can thus be used as an indicator of a position of the second medical device with respect to the first medical device. Accordingly, by sensing the output voltage, it can be determined, for example, whether a perforating tip of a needle is approaching a distal end of the catheter, or has passed beyond a distal end of the catheter. This can facilitate ease of use of the medical devices, and enhance patient safety.

Figure 1:
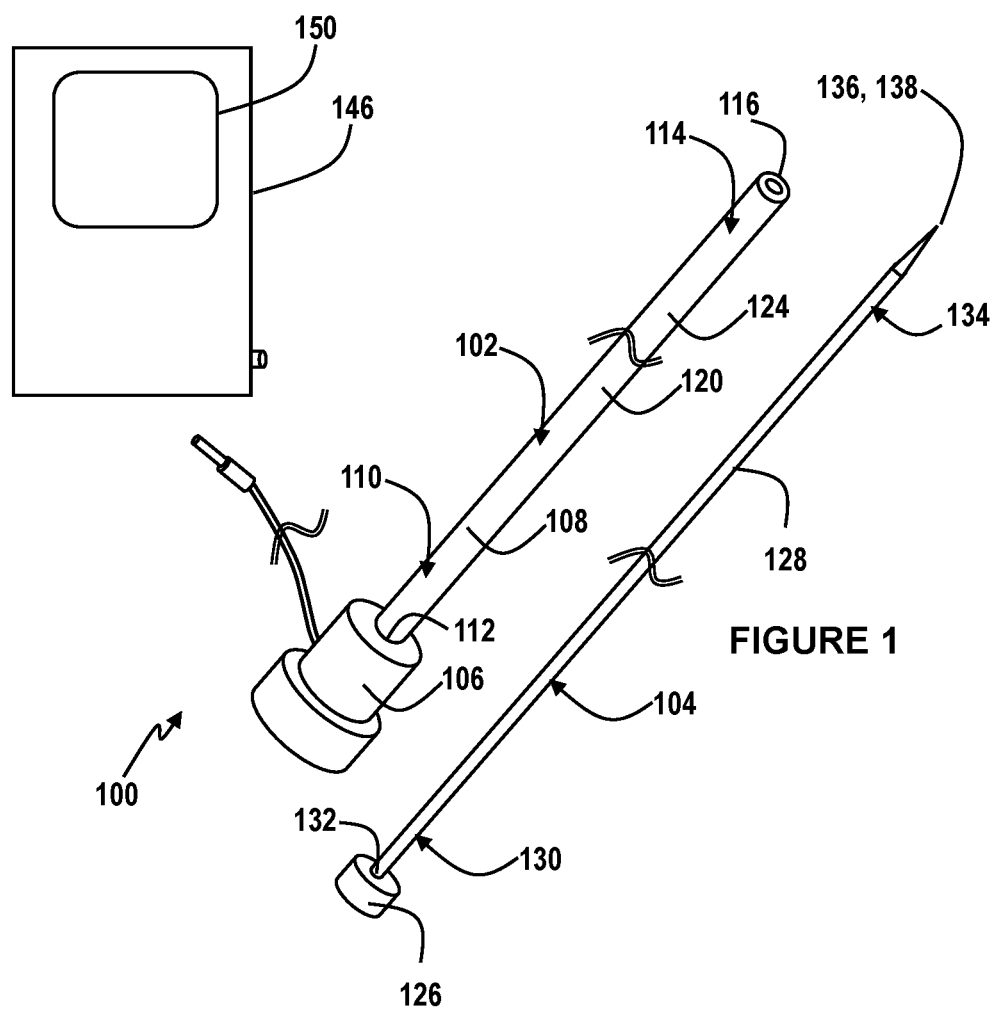
FIG. 1 is a perspective view of a first example system of medical devices, showing a first medical device, second medical device, and control unit, spaced apart and disconnected from each other.
Figure 2:
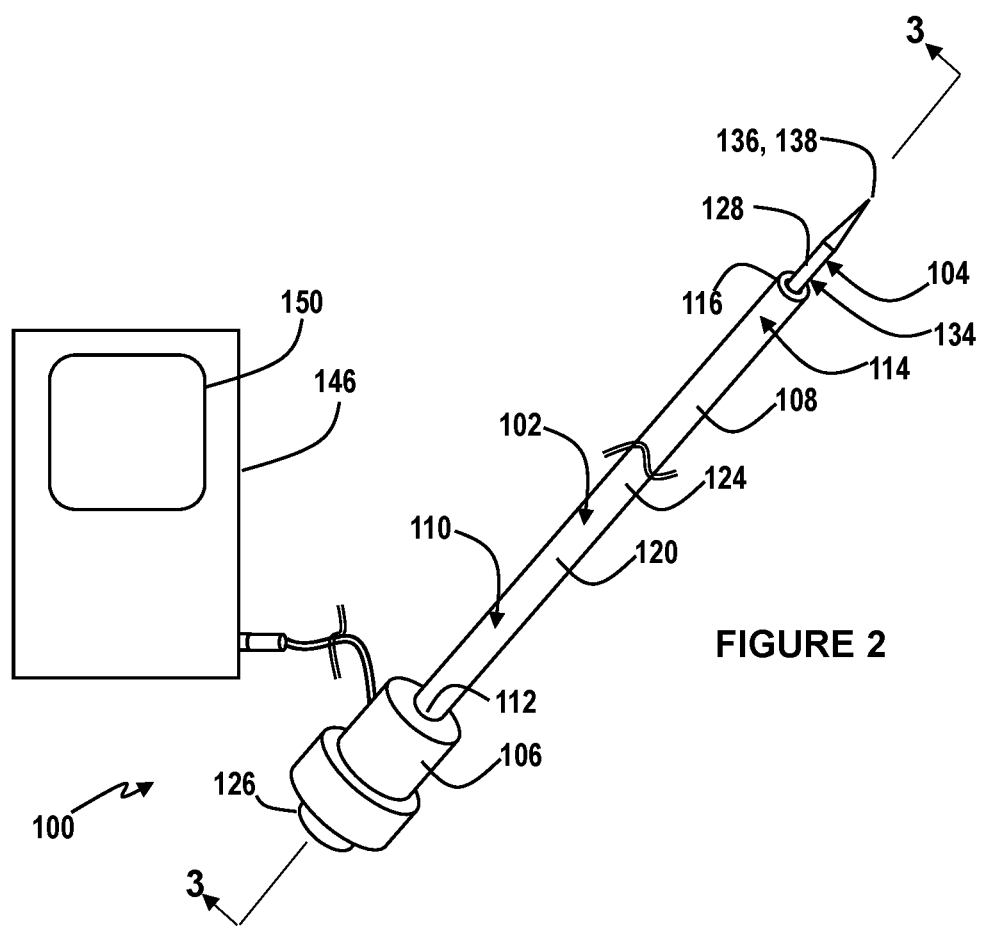
FIG. 2 is a perspective view of the system of FIG. 1, showing the second medical device inserted into the first medical device, and the first medical device connected to the control unit.

Referring now to FIGS. 1 and 2, a first example system 100 of medical devices is shown. In the example shown, the system 100 includes a first medical device 102 in the form of a catheter, and a second medical device 104 in the form of a perforation device. The catheter can be, for example, a sheath, a dilator, or an alternative device that is intended for use by passing another medical device therethrough (e.g. coaxially therethrough). The perforation device can be, for example, a mechanical perforation device, or a radiofrequency (RF) perforation device. In alternative examples, the second medical device can be alternative type of medical device that is intended for use by being passed through another medical device.

Figure 3:
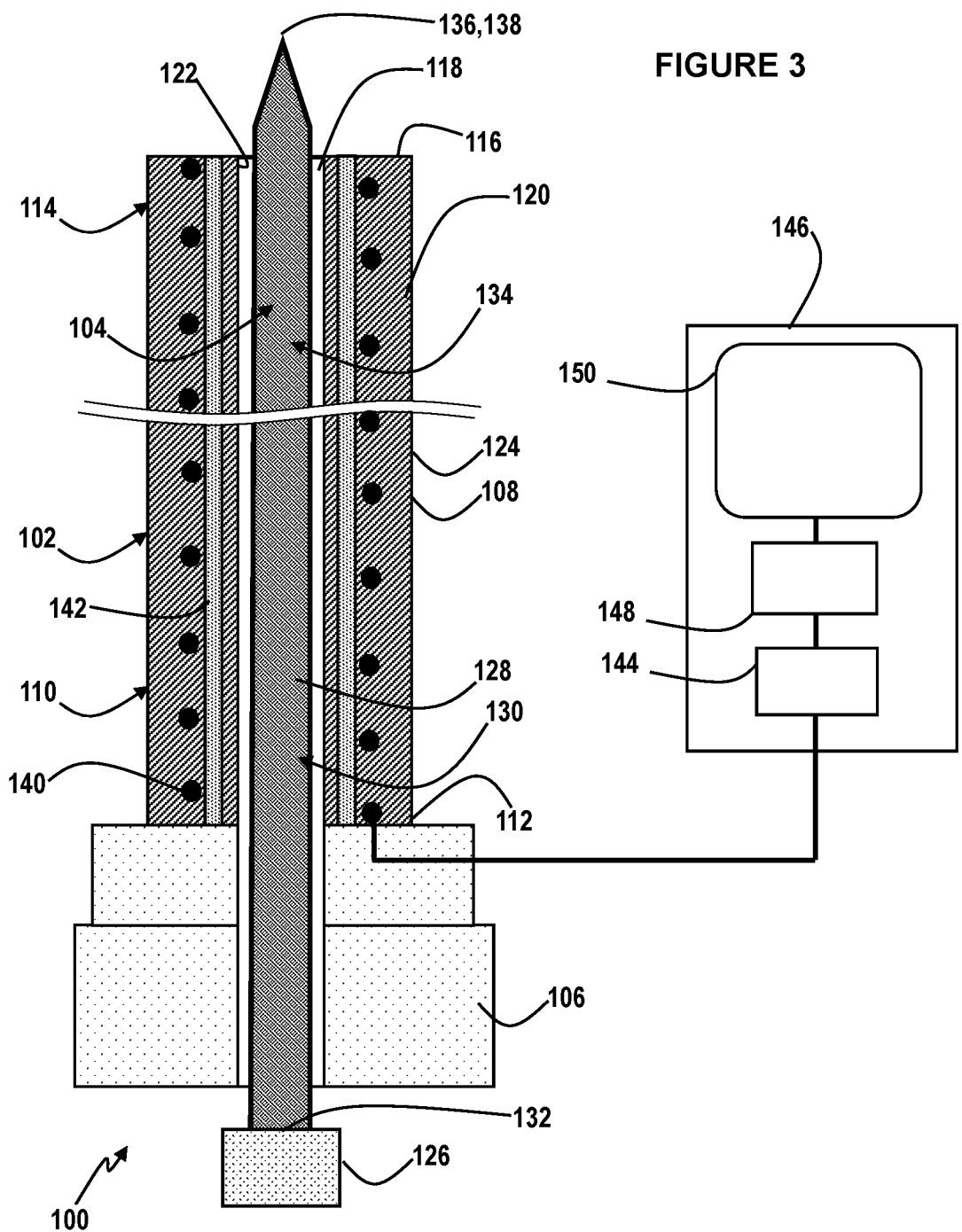
FIG. 3 is a longitudinal cross section taken along line 3-3 in FIG. 2, schematically showing the control unit and related parts.

Referring also to FIG. 3, in the example shown, the first medical device 102 includes a hub 106 and an elongate member 108 extending from the hub 106. The elongate member 108 has a proximal portion 110 defining a proximal end 112 of the elongate member 108, a distal portion 114 defining a distal end 116 of the elongate member 108, and a lumen 118 (shown in FIG. 3) extending longitudinally through the elongate member 108 from the proximal end 112 to the distal end 116. The elongate member 108 includes a sidewall 120, which extends longitudinally between the proximal end 112 and the distal end 116, and radially between an inner surface 122 (shown in FIG. 3) that defines the lumen 118, and an outer surface 124. The sidewall 120 can be made from an electrically insulating material, such as an electrically insulating polymer (e.g. polyurethane).

Referring still to FIGS. 1 to 3, in the example shown, the second medical device 104 includes a hub 126 and a needle 128 extending from the hub 126. The needle 128 is electrically conductive (e.g. is metallic). The needle 128 has a proximal portion 130 defining a proximal end 132 of the needle 128, and a distal portion 134 defining a distal end 136 of the needle 128. The distal end 136 of the needle 128 includes a perforating tip 138. As shown in FIG. 2, the needle 128 is advanceable through the hub 106 and through the lumen 118, from the proximal end 112 of the elongate member 108 towards the distal portion 114 of the elongate member 108, to position the perforating tip 138 of the needle 128 proud of the distal end 116 of the elongate member 108.

Referring to FIG. 3, the system 100 further includes an inductor, which in the example shown includes a coil 140, and a magnetic core 142. The inductor is part of an RLC circuit. RLC circuits in general are known in the art, and are not described in detail herein. Briefly, in addition to the inductor, the RLC circuit further includes a resistor and a capacitor, as well as an excitation voltage source and an output voltage sensor. The parts of the RLC circuit, other than the inductor, are shown collectively at 144 in FIG. 3.

Referring still to FIG. 3, in the example shown, the coil 140 is supported by the first medical device 102, and is wound around the lumen 118. As used herein, the term "supported by" indicates that the coil is integral with, embedded in, connected to, mounted to, adhered to, affixed to, or otherwise secured to the first medical device 102, so that the coil moves with the first medical device 102. In the example shown, the coil is embedded in the sidewall 120. The coil 140 can be, for example, a wire such as copper wire.

Referring still to FIG. 3, in the example shown, the magnetic core 142 is positioned within the coil 140 and is also supported by the first medical device 102. In the example shown, the magnetic core 142 is embedded in the sidewall 120, radially inwardly of the coil 140. The magnetic core 142 can be, for example, a magnetic tape that is wound around the lumen 118 and embedded in the sidewall 120.

Referring still to FIG. 3, in the example shown, the coil 140 and magnetic core 142 extend continuously from the proximal portion 110 to the distal portion 114 of the elongate member 108. In alternative examples, a coil and/or magnetic core can extend along less than the entire length of the elongate member, such as along a majority of the length of the elongate member, or along only a small section of the elongate member. For example, a coil and magnetic core can be relatively short in length, and can be positioned within the distal portion of the elongate member, proximate the distal end (e.g. right at the distal end, or slightly proximal of the distal end).

Referring still to FIG. 3, the system further includes a control unit 146. The control unit 146 houses the components of the RLC circuit other than the inductor (i.e. the excitation voltage source, a resistor, a capacitor, and an output voltage sensor, shown at 144), which are electrically connected to the coil 140 to complete the RLC circuit. The coil 140 can optionally be removably electrically connected to the control unit 146, for example with a male connector (shown in FIG. 1) that can connect to a female connector of the control unit 146.

Figure 4:
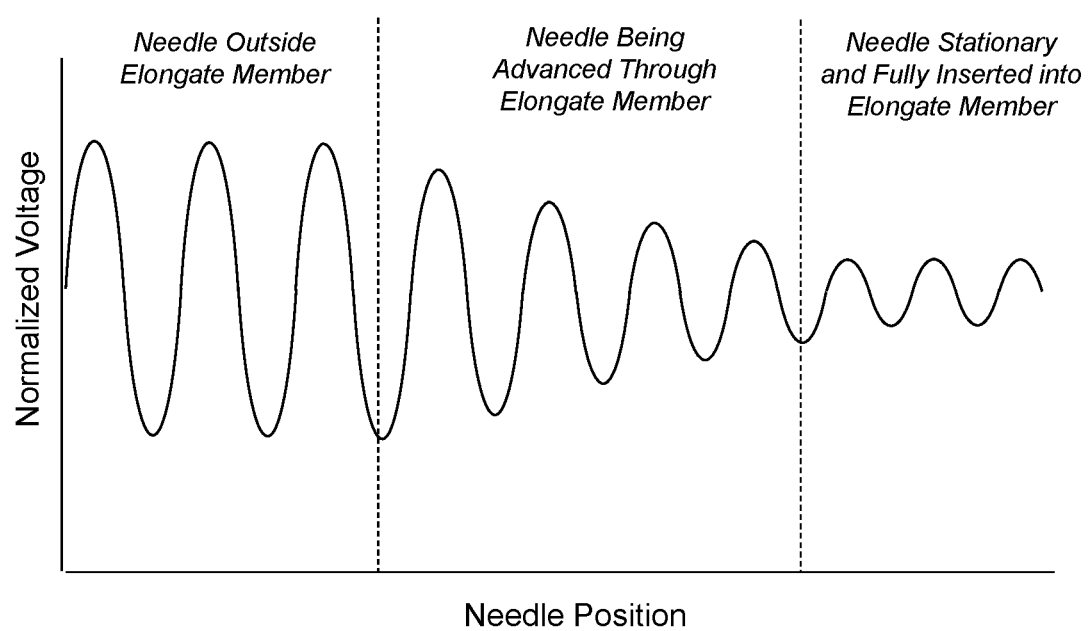
FIG. 4 is a simplified graph showing the change in output voltage as the second medical device of FIGS. 1 to 3 is advanced through the first medical device of FIGS. 1 to 3.

The control unit further 146 houses a processor 148, and an output device 150, described in further detail below In use, an excitation voltage can be applied to the RLC circuit from the excitation voltage source as the needle 128 approaches and is advanced through the lumen 118. The excitation voltage can be tuned so that, in the absence of the needle 128 in the lumen 118, the circuit is resonant. The output voltage of the RLC circuit can be sensed as the needle 128 approaches and is advanced through the lumen 118. As the needle 128 enters and is advanced in the lumen 118, the inductance of the RLC circuit will change due to the presence of the needle 128. As shown in FIG. 4, the change in inductance will cause the output voltage of the RLC circuit to change—i.e. it can become non-resonant. The output voltage can thus be used as an indicator of the longitudinal position of the needle 128 with respect to the elongate member 108. For example, the output voltage can be an indicator of when the perforating tip 138 is well shrouded within the elongate member 108 (and thus when a patient's anatomy is protected from being perforated by the needle 128), or when the perforating tip 138 is at the distal end 116 of the elongate member 108 (i.e. when the needle 128 is 'primed' for use), or when the perforating tip 138 has passed beyond the distal end 116 of the elongate member 108 and is exposed (and thus when a patient's anatomy is not protected from being perforated by the needle 128).

Referring back to FIG. 3, the voltage sensor of the RLC circuit is in communication with the processor 148, and the processor 148 is in communication with the output device 150. The output voltage sensor senses the output voltage of the RLC circuit, and can generate a signal (referred to herein as a "sensor signal") based on the sensed output voltage. The processor 148 can include various components (e.g. an analog to digital converter, isolation circuitry, and a microcontroller), and is configured to receive and process the signal from the output voltage sensor, and to generate a signal (referred to herein as a "processor signal") based on the sensor signal. The output device 150 can receive the processor signal, and can generate an output based on the processor signal.

In some examples, the output device 150 can include a light, and the processor signal can cause illumination of the light, or a change in color of the light. For example, when the sensor signal indicates that the output voltage has reached a predetermined value that corresponds to the perforating tip 138 being at a predetermined longitudinal position with respect to the elongate member 108 (e.g. the perforating tip being at the distal end 116 of the elongate member 108), the processor 148 can signal the output device 150 to change the color of the light from green to red.

In some examples, the output device 150 can include a screen that shows a graphical user interface (GUI). The processor signal can cause the output device 150 to generate an image showing the longitudinal position of the needle 128 within the elongate member 108. For example, as the needle 128 is advanced through lumen 118 and the output voltage changes, the image can change based on the output voltage.

Figure 5:
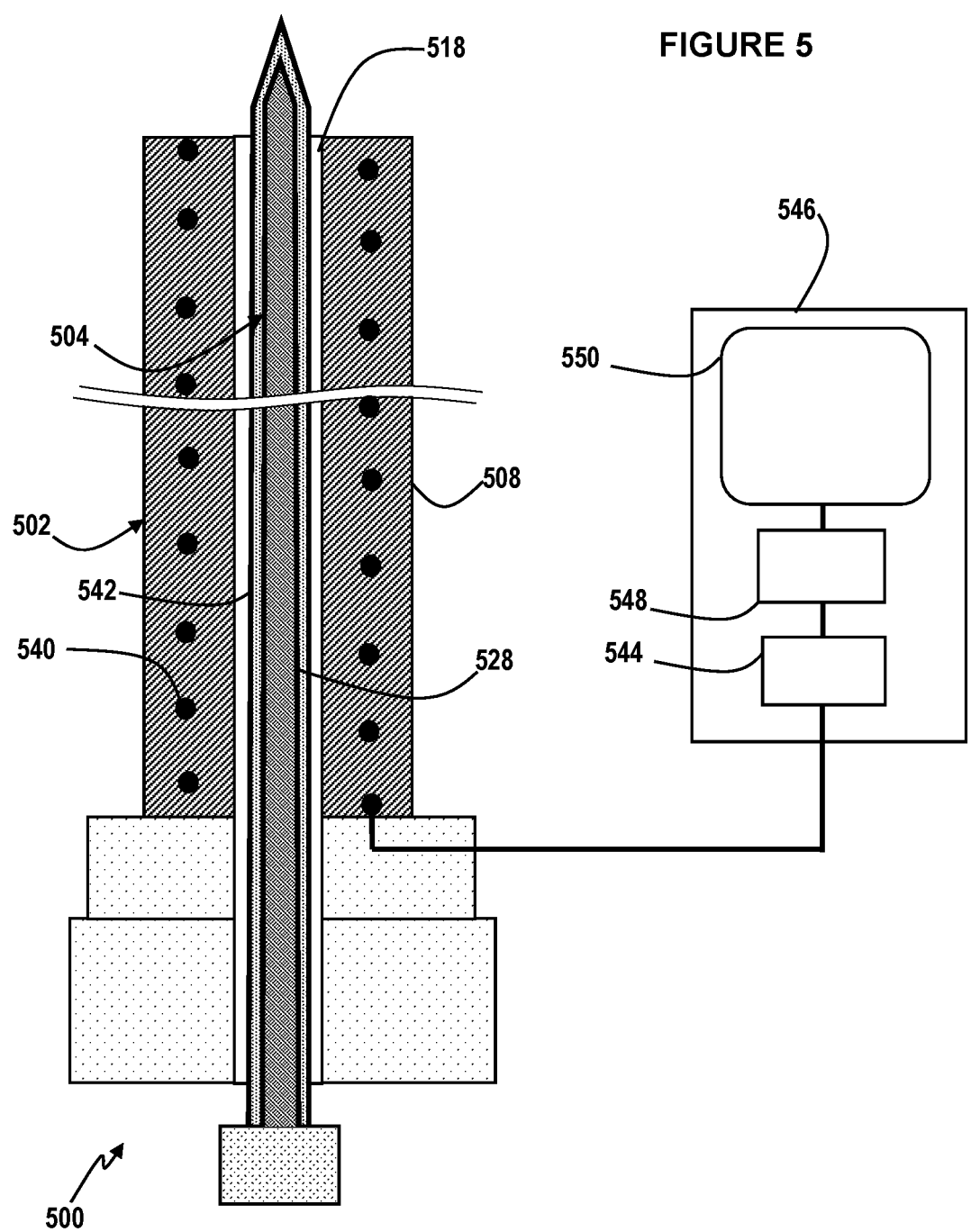
FIG. 5 is a cross-section similar to that of FIG. 3, showing a first medical device, second medical device, and control unit of a second example system.

Referring now to FIG. 5, an alternative example system is shown. In the example of FIG. 5, features that are like those of FIGS. 1 to 3 will be referred to with like reference numerals, incremented by 400.

The system 500 of FIG. 5 is similar to the system 100 of FIGS. 1 to 3, and includes a first medical device 502 in the form of a catheter having an elongate member 508 with a lumen 518, a second medical device 504 including a needle 528 that is advanceable through the lumen 518, and a control unit 546, which houses a processor 548 and an output device 550. The system 500 further includes an inductor, which is part of an RLC circuit. The RLC circuit further includes an excitation voltage source, a resistor, a capacitor, and an output voltage sensor, which are shown collectively at 544 in FIG. 5. In the example of FIG. 5, the inductor includes a coil 540, and a magnetic core 542; however the magnetic core 542 of the inductor is provided by the needle 528, which includes a coating of a magnetic material (e.g. a coating of epoxy containing suspended ferrites or magnetic tape).

Figure 6:
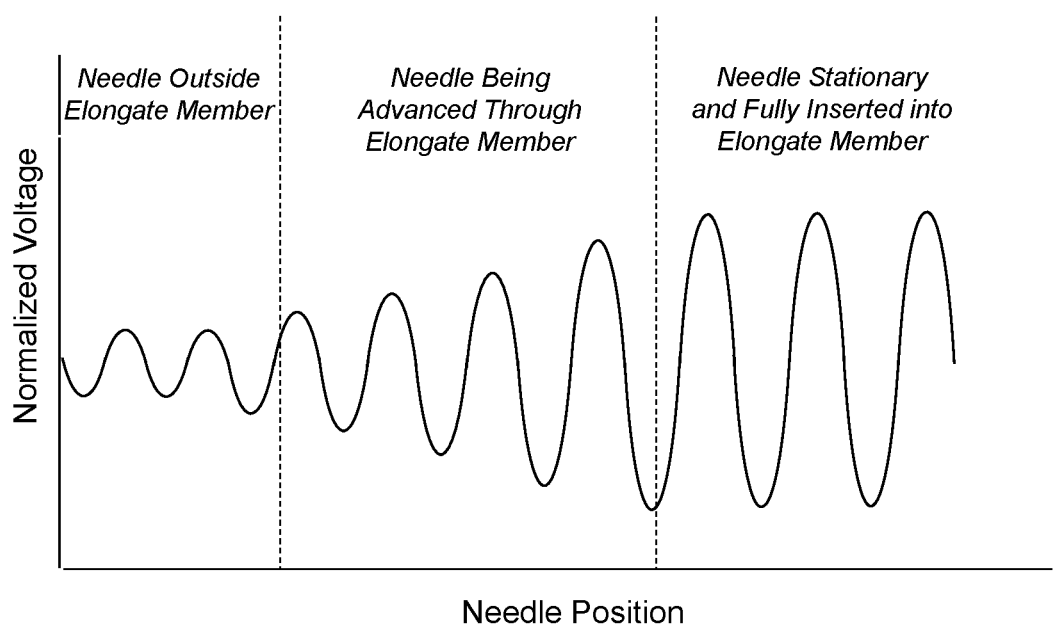
FIG. 6 is a simplified graph showing the change in output voltage as the second medical device of FIG. 5 is advanced through the first medical device of FIG. 5.

In use, an excitation voltage can be applied to the RLC circuit from the excitation voltage source as the needle 528 approaches and is advanced through the lumen 518. The excitation voltage can be tuned so that, when the needle 528 is fully inserted into the elongate member 508, the circuit is resonant. The output voltage of the RLC circuit can be sensed as the needle 528 approaches and is advanced through the lumen 518. As the needle 528 enters and is advanced in the lumen 518, the inductance of the RLC circuit will change due to the presence of the needle 528. As shown in FIG. 6, the change in inductance will cause the output voltage of the RLC circuit to change—i.e. it will become resonant. Similarly to the example of FIGS. 1 to 3, the output voltage can thus be used as an indicator of the longitudinal position of the needle 528 with respect to the elongate member 508.

Figure 7:
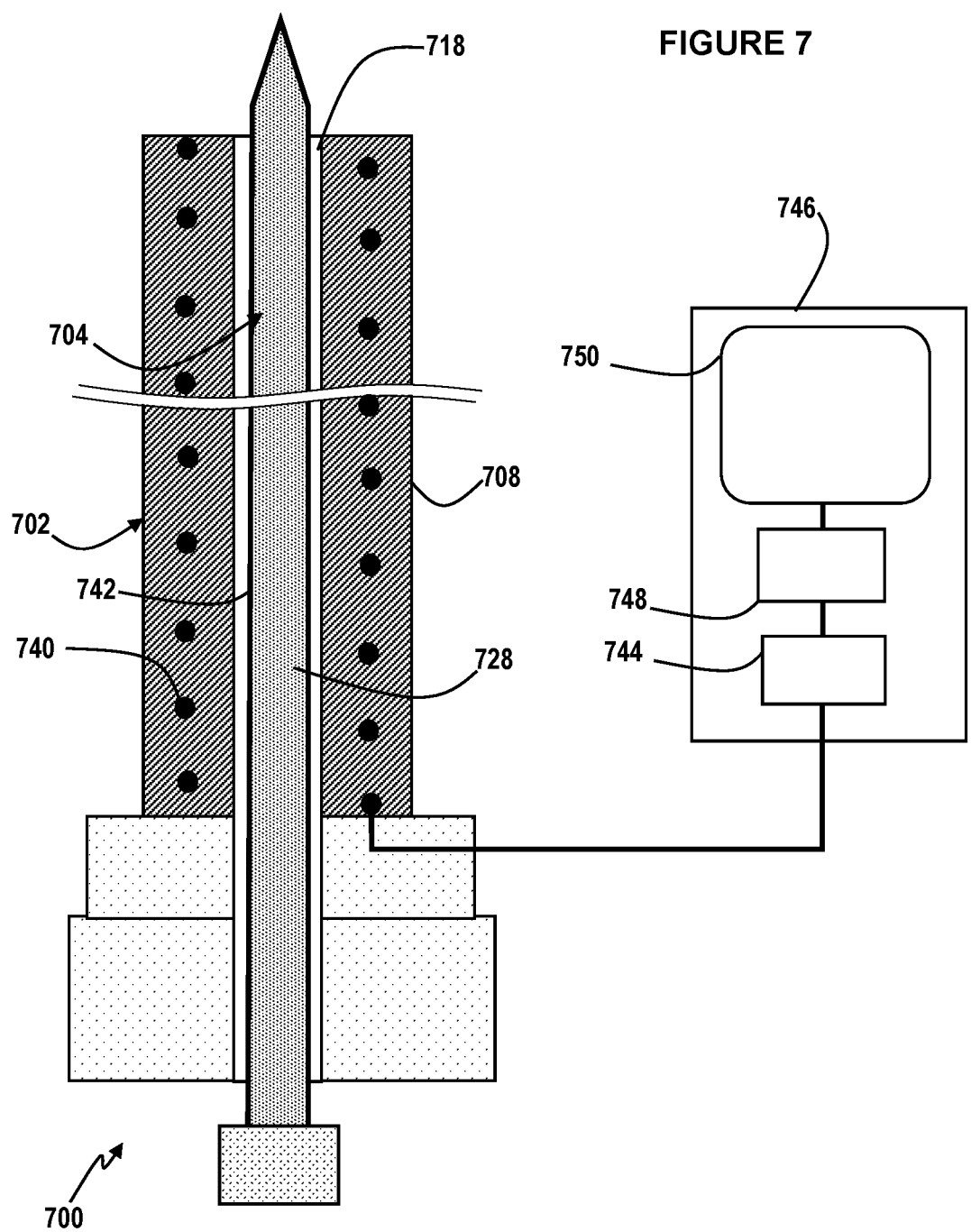
FIG. 7 is a cross-section similar to that of FIG. 3, showing a first medical device, second medical device, and control unit of a third example system.

Referring now to FIG. 7, another alternative example system is shown. In the example of FIG. 7, features that are like those of FIGS. 1 to 3 will be referred to with like reference numerals, incremented by 600.

The system 700 of FIG. 7 is similar to the system 500 of FIG. 5, and includes a first medical device 702 in the form of a catheter having an elongate member 708 with lumen 718, a second medical device 704 including a needle 728 that is advanceable through the lumen 718, and a control unit 746, which houses a processor 748 and an output device 750. The system 700 further includes an inductor, which is part of an RLC circuit. The RLC circuit further includes an excitation voltage source, a resistor, a capacitor, and an output voltage sensor, which are shown collectively at 744 in FIG. 7. Similarly to the example of FIG. 5, the inductor includes a coil 740, and a magnetic core 742 that is provided by the needle 728; however, in the example of FIG. 7, the needle 728 is fabricated from a magnetic material, such as silicon steel, manganese-zinc ferrite, iron, etc., so that the needle 728 as a whole is magnetic.

The system of FIG. 7 can be operated similarly to the system of FIG. 5—i.e. the excitation voltage can be tuned so that, when the needle 728 is fully inserted into the elongate member 708, the circuit is resonant. The output voltage can thus be used as an indicator of the longitudinal position of the needle 728 with respect to the elongate member 708.

Figure 8:
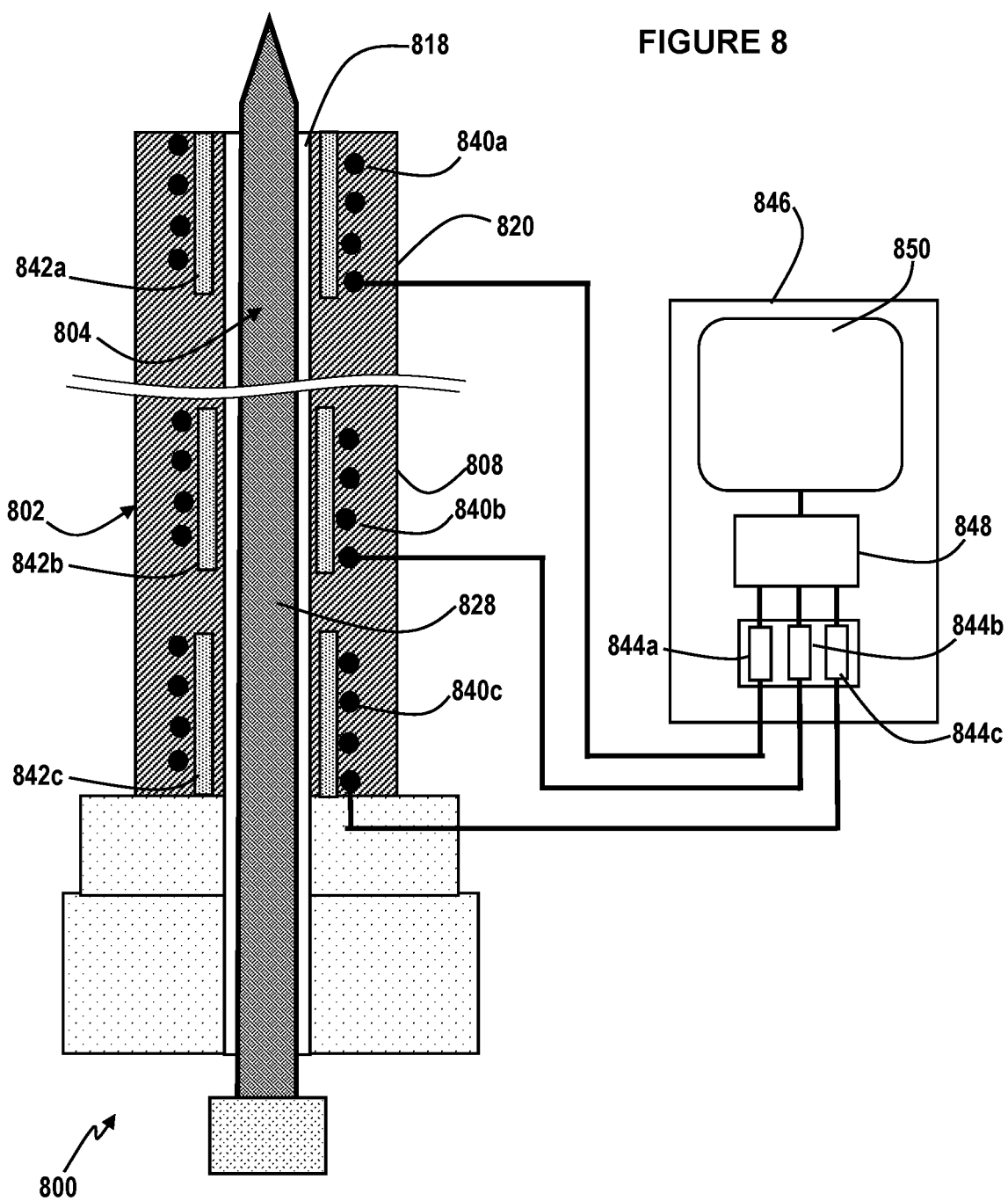
FIG. 8 is a cross-section similar to that of FIG. 3, showing a first medical device, second medical device, and control unit of a fourth example system.

Referring now to FIG. 8, another alternative example system is shown. In the example of FIG. 8, features that are like those of FIGS. 1 to 3 will be referred to with like reference numerals, incremented by 700.

The system 800 of FIG. 8 is similar to the system 100 of FIGS. 1 to 3, and includes a first medical device 802 in the form of a catheter having a lumen 818, a second medical device 804 including a needle 828 that is advanceable through the lumen 818, and a control unit 846, which houses a processor 848 and an output device 850.

The system 800 of FIG. 8 includes a plurality of RLC circuits (three of which are shown). Each RLC circuit includes an inductor that includes a coil and a magnetic core (i.e. the first RLC circuit includes a first coil 840a and a first magnetic core 842a; the second RLC circuit includes a second coil 840b and a second magnetic core 842b; and the third RLC circuit includes a third coil 840c and a third magnetic core 842c). Each coil 840a, 840b, 840c is embedded in the sidewall 820, and each magnetic core 842a, 842b, 842c is embedded in the sidewall 820 radially inwardly of the coils 840a, 840b, 840c, respectively. The inductors are longitudinally spaced apart so that the second inductor is spaced proximally from the first inductor, and the third inductor is spaced proximally from the second inductor. The first RLC circuit further includes an excitation voltage source, a resistor, a capacitor, and an output voltage sensor, which are shown collectively at 844a in FIG. 8; the second RLC circuit further includes an excitation voltage source, a resistor, a capacitor, and an output voltage sensor, which are shown collectively at 844b in FIG. 8; and the third RLC circuit further includes an excitation voltage source, a resistor, a capacitor, and an output voltage sensor, which are shown collectively at 844c in FIG. 8.

Figure 9:
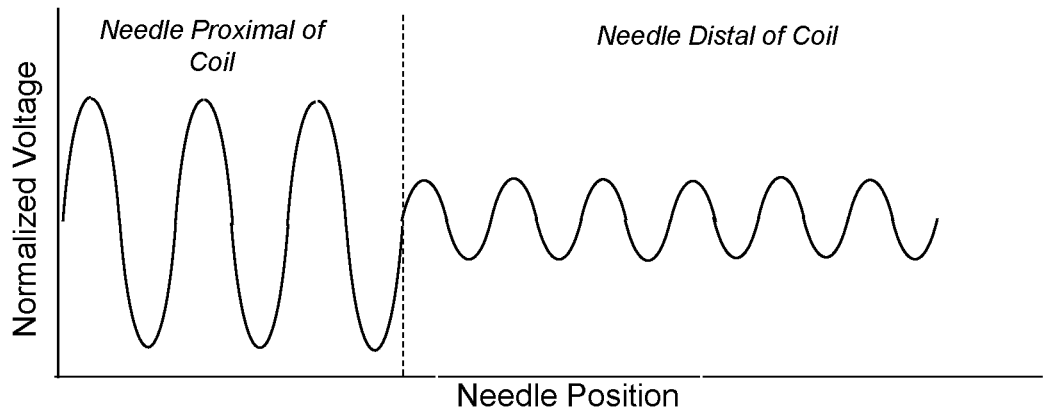
FIG. 9 is a simplified graph showing the change in output voltage as the second medical device of FIG. 8 is advanced through the first medical device of FIG. 8.
Figure 9:
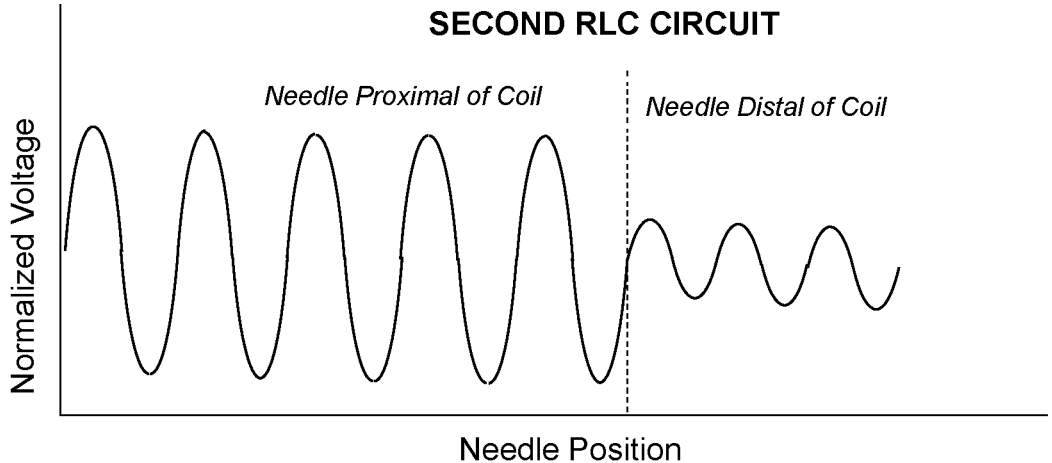
Figure 9:
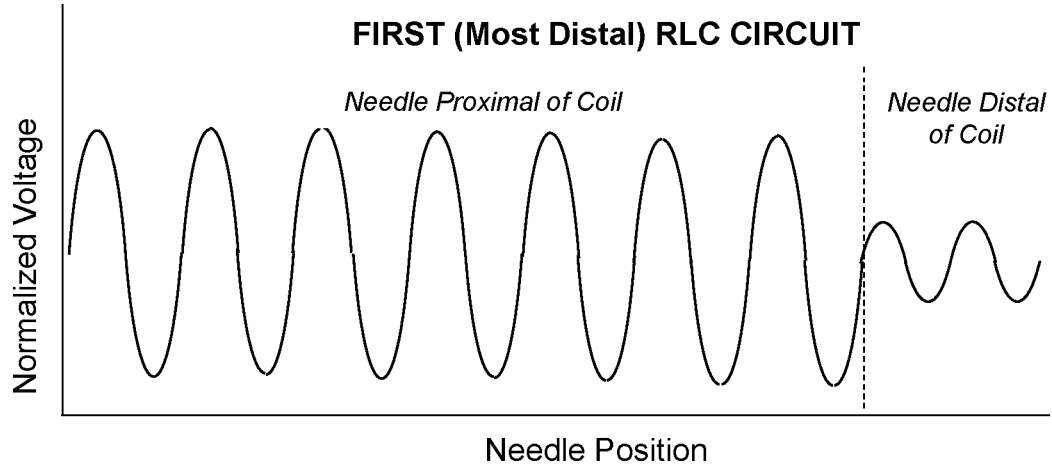

In use, an excitation voltage can be applied to each RLC circuit from the respective excitation voltage source as the needle 828 approaches and is advanced through the lumen 818. In use, each RLC circuit can be tuned so that a drop in signal amplitude occurs as the needle 828 passes the inductor of that circuit. The output voltage of each RLC circuit can be sensed as the needle 828 approaches and is advanced through the lumen 818. As the needle 828 enters and is advanced into the lumen 818, the inductance of each RLC circuit will change due to the presence of the needle 828. As shown in FIG. 9, the change in inductance will cause the output voltage of each RLC circuit to change—i.e. it will become non-resonant as the needle 828 passes by that inductor. The output voltage of each RLC circuit can thus be used as an indicator of the longitudinal position of the needle 828 with respect to the elongate member 808.

Figure 10:
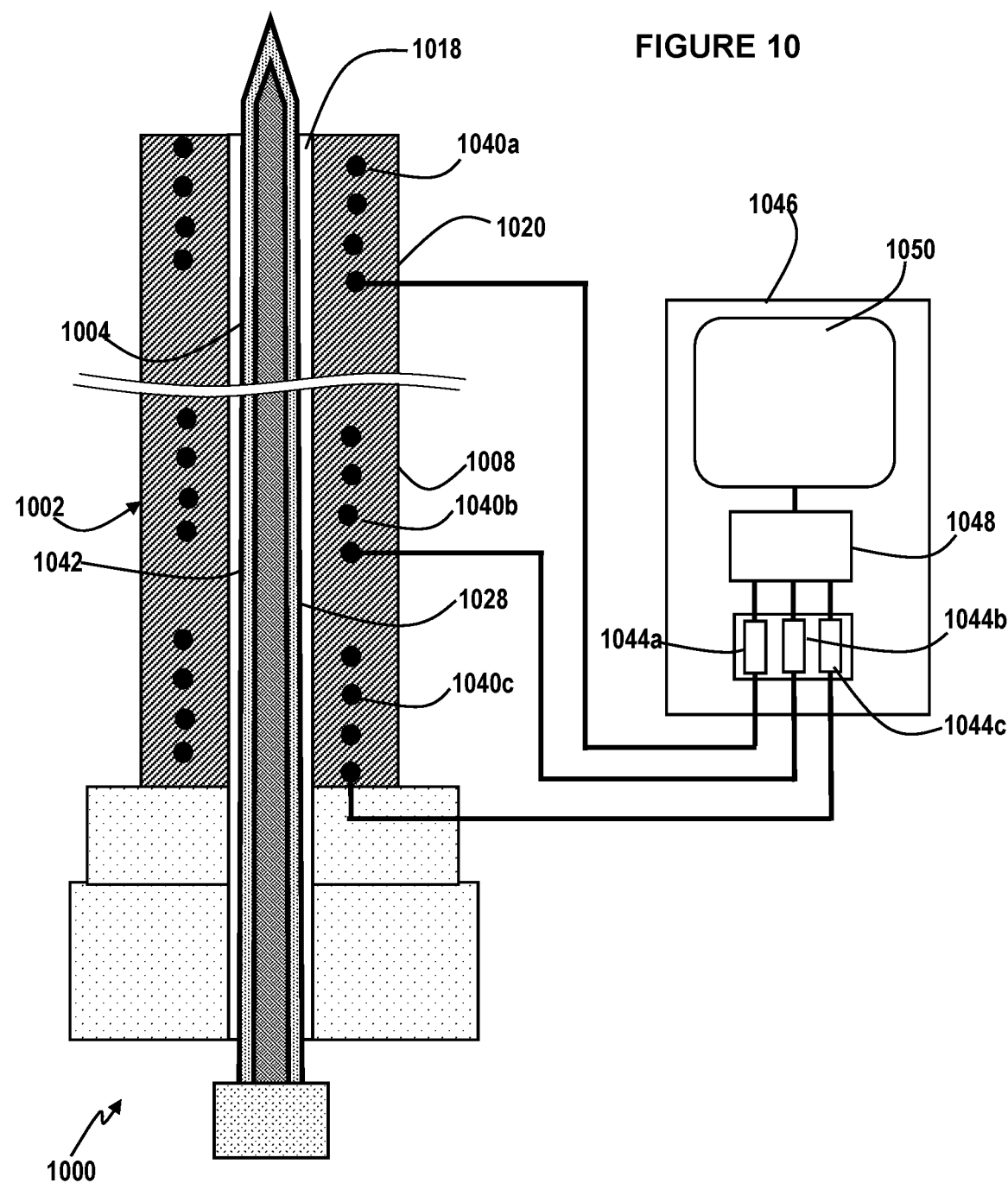
FIG. 10 is a cross-section similar to that of FIG. 3, showing a first medical device, second medical device, and control unit of a fifth example system.

Referring now to FIG. 10, another alternative example system is shown. In the example of FIG. 10, features that are like those of FIGS. 1 to 3 will be referred to with like reference numerals, incremented by 900.

The system 1000 of FIG. 10 includes a first medical device 1002 in the form of a catheter having an elongate member 1008 with a lumen 1018, a second medical device 1004 including a needle 1028 that is advanceable through the lumen 1018, and a control unit 1046, which houses a processor 1048 and an output device 1050. The system 1000 of FIG. 10 is similar to the system 800 of FIG. 8, in that the system 1000 of FIG. 10 includes a plurality of RLC circuits (three of which are shown). Each RLC circuit includes an inductor that includes a coil that is embedded in the sidewall 1020 (i.e. the first RLC circuit includes a first coil 1040a; the second RLC circuit includes a second coil 1040b; and the third RLC circuit includes a third coil 1040c). The coils 1040a, 1040b, 1040c are longitudinally spaced apart so that the second coil 1040b is spaced proximally from the first coil 1040a, and the third coil 1040c is spaced proximally from the second coil 1040b.

The first RLC circuit further includes an excitation voltage source, a resistor, a capacitor, and an output voltage sensor, which are shown collectively at 1044a in FIG. 10; the second RLC circuit further includes an excitation voltage source, a resistor, a capacitor, and an output voltage sensor, which are shown collectively at 1044b in FIG. 10; and the third RLC circuit further includes an excitation voltage source, a resistor, a capacitor, and an output voltage sensor, which are shown collectively at 10044c in FIG. 8.

Similarly, to the system of FIG. 5, in the system of FIG. 10, the magnetic core 1042 of each inductor is provided by the needle 1028, which includes a coating of a magnetic material (e.g. a coating of epoxy containing suspended ferrites or magnetic tape).

Figure 11:
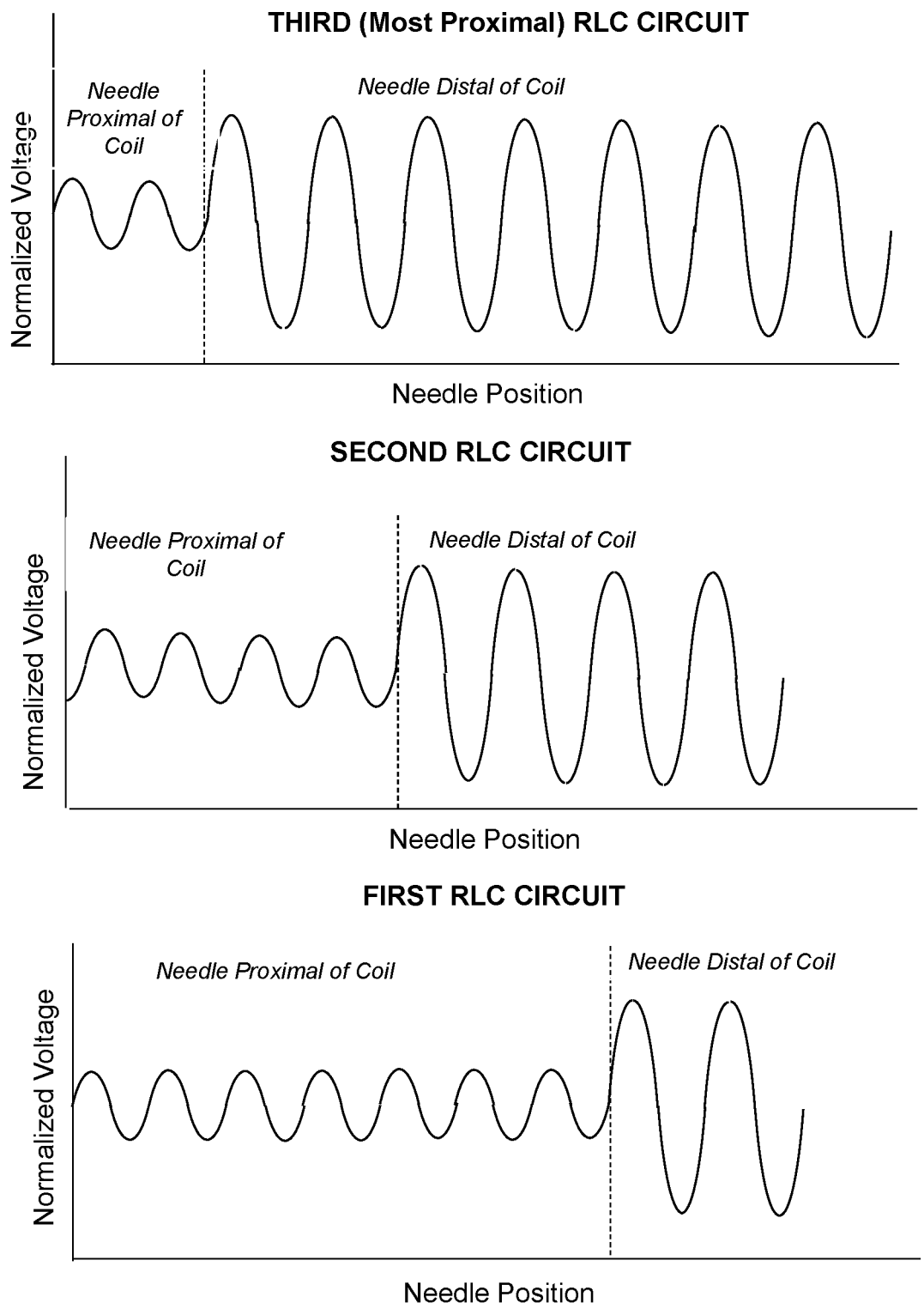
FIG. 11 is a simplified graph showing the change in output voltage as the second medical device of FIG. 10 is advanced through the first medical device of FIG. 10.

In use, an excitation voltage can be applied to each RLC circuit from the respective excitation voltage source as the needle 1028 approaches and is advanced through the lumen 1018. Each RLC circuit can be tuned so that the circuit becomes resonant as the needle 1028 passes the inductor of that circuit. The output voltage of each RLC circuit can be sensed as the needle 1028 approaches and is advanced through the lumen 1018. As the needle 1028 enters and is advanced into the lumen 1018, the inductance of each RLC circuit will change due to the presence of the needle 1028. As shown in FIG. 11, the change in inductance will cause the output voltage of each RLC circuit to change—i.e. it will become resonant as the needle 1028 passes by that inductor. The output voltage of each RLC circuit can thus be used as an indicator of the longitudinal position of the needle 1028 with respect to the elongate member 1008.

Figure 12:
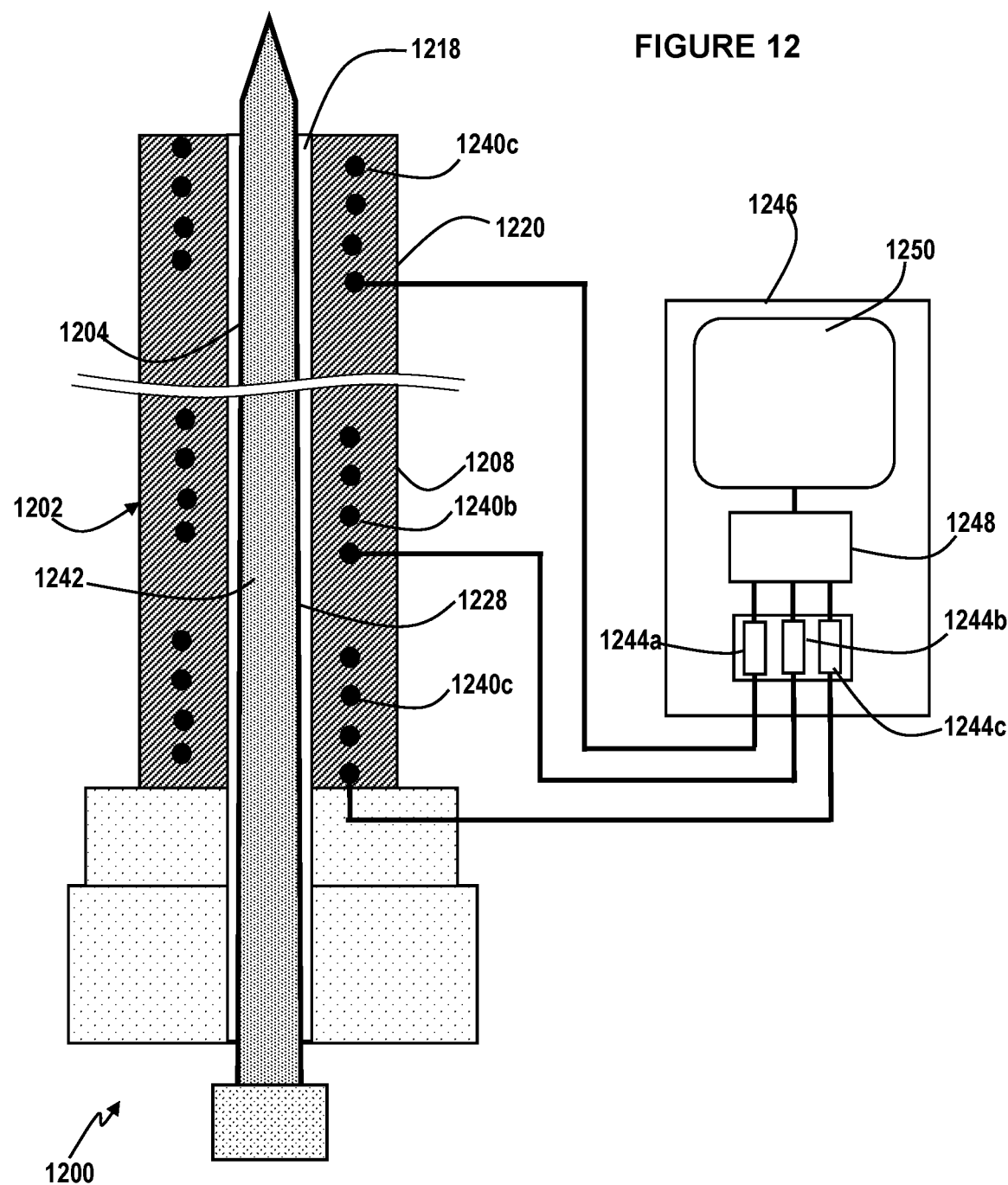
FIG. 12 is a cross-section similar to that of FIG. 3, showing a first medical device, second medical device, and control unit of a sixth example system.

Referring now to FIG. 12, another alternative example system is shown. In the example of FIG. 12, features that are like those of FIGS. 1 to 3 will be referred to with like reference numerals, incremented by 1100.

The system 1200 of FIG. 12 is similar to the system 1000 of FIG. 10, and includes a first medical 1202 device in the form of a catheter having an elongate member 1208 with a lumen 1218, a second medical device 1204 including a needle 1228 that is advanceable through the lumen 1218, and a control unit 1246, which houses a processor 1248 and an output device 1250.

Similarly to the system 1000 of FIG. 10, the system 1200 includes a plurality of RLC circuits (three of which are shown). Each RLC circuit includes an inductor that includes a coil that is embedded in the sidewall 1220 (i.e. the first RLC circuit includes a first coil 1240*a*; the second RLC circuit includes a second coil 1240*b*; and the third RLC circuit includes a third coil 1240*c*). The coils 1240*a*, 1240*b*, 1240*c* are longitudinally spaced apart so that the second coil 1240*b* is spaced proximally from the first coil 1240*a*, and the third coil 1240*c* is spaced proximally from the second coil 1240*b*.

Similarly to the system 1000 of FIG. 10, each inductor includes a magnetic core 1242 that is provided by the needle 1228; however, in the system 1200 of FIG. 12, the needle is fabricated from a magnetic material, such as silicon steel, manganese-zinc ferrite, iron, etc, so that the needle 1228 as a whole is magnetic.

The system 1200 of FIG. 12 can be operated similarly to the system 1000 of FIG. 10—i.e. the excitation voltage can be tuned so that, when the needle 1228 is fully inserted into the elongate member 1208, the circuit is resonant, and the output voltage can thus be used as an indicator of the longitudinal position of the needle 1228 with respect to the elongate member 1208.

The devices and systems described above can be used in various medical procedures, but may be particularly useful in transseptal perforation procedures, in which a dilator (i.e. a first medical device) is advanced via the femoral vein towards the heart and positioned adjacent the fossa ovalis of the atrial septum, and then a transseptal perforation device (i.e. a second medical device) is advanced into and through the lumen of the dilator, from the proximal end of the dilator towards the distal end of the dilator. In such procedures, as the transseptal perforation device is advanced through the lumen of the dilator, an excitation voltage can be applied to the RLC circuit(s), and the output voltage of the RLC circuit(s) can be sensed and monitored, to provide an indicator of the longitudinal position of the transseptal perforation device with respect to the dilator.

As described above, an output can be generated based on the output voltage, to provide an indication of the longitudinal position of the transseptal perforation device with respect to the dilator. The output can be, for example, in the form of an image, or a light. This can help an operator to ensure that the perforating tip of the perforation device is shrouded within the dilator until it is ready for use by the operator.

Optionally, based on the output, the position of the transseptal perforation device can be adjusted with respect to the dilator. For example, if a red light illuminates before the user is ready to perforate the fossa ovalis, the user can withdraw the transseptal perforation device proximally, until a green light illuminates.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

What is claimed is:

1. A medical device comprising:
an elongate member having a proximal portion defining a proximal end, a distal portion defining a distal end, a sidewall extending longitudinally between the proximal end and the distal end and radially between an inner surface and an outer surface, and a lumen defined by the inner surface and extending longitudinally through the elongate member from the proximal end to the distal end;
an inductor comprising a coil embedded in the sidewall and wound around the lumen;
an excitation voltage source;
a resistor;
a capacitor; and
an output voltage sensor;
wherein the coil is electrically connectable to the excitation voltage source, the resistor, the capacitor, and the output voltage sensor to form an RLC circuit.

2. The medical device of claim 1, wherein the inductor further comprises a magnetic core positioned radially inwardly of the coil and supported by the elongate member.

3. The medical device of claim 2, wherein the magnetic core is embedded in the sidewall.

4. The medical device of claim 1, wherein the coil extends continuously from the proximal portion to the distal portion.

5. The medical device of claim 1, wherein the coil is positioned within the distal portion, proximate the distal end.

6. The medical device of claim 1, further comprising a second inductor, the second inductor comprising a second coil embedded in the sidewall and wound around the lumen, wherein the second coil is spaced proximally from the coil of the RLC circuit, and wherein the second coil is electrically connectable to a second excitation voltage source, a second resistor, and a second output voltage sensor to form a second RLC circuit.

7. The medical device of claim 1, further comprising a second medical device comprising a needle advanceable through the lumen from the proximal end towards the distal end, whereby as the needle is advanced through the lumen, an output voltage of the RLC circuit is an indicator of a longitudinal position of the needle with respect to the elongate member, and wherein the voltage sensor is configured to sense the output voltage of the RLC circuit and generate a sensor signal based on the output voltage.

8. The medical device of claim 7, further comprising a processor in communication with the voltage sensor and configured to receive and process the sensor signal from the voltage sensor, and generate a processor signal based on the sensor signal.

9. The medical device of claim 8, further comprising an output device in communication with the processor and configured to receive the processor signal and generate an output based on the processor signal, wherein the output is an indicator of the longitudinal position of the needle with respect to the elongate member.

10. The medical device of claim 9, wherein the output device comprises at least one of a light and a display.

11. The medical device of claim 10, wherein the output comprises illumination of the light when the needle is at a predetermined longitudinal position with respect to the elongate member.

12. The medical device of claim 7, wherein the inductor further comprises a magnetic core, and the magnetic core is provided by a magnetic coating on the needle.

13. The medical device of claim 1, wherein the coil extends continuously from the proximal portion to the distal portion.

\* \* \* \* \*